US00PP29333P3

(12) United States Plant Patent
Baglin

(10) Patent No.: US PP29,333 P3
(45) Date of Patent: May 29, 2018

(54) ***DIETES* PLANT NAMED 'DI2'**

(50) Latin Name: *Dietes bicolor*
Varietal Denomination: DI2

(71) Applicant: Katrina Baglin, Richmond (AU)

(72) Inventor: Katrina Baglin, Richmond (AU)

( * ) Notice: Subject to any disclaimer, the term of this patent is extended or adjusted under 35 U.S.C. 154(b) by 77 days.

(21) Appl. No.: 14/999,046

(22) Filed: Mar. 23, 2016

(65) Prior Publication Data

US 2017/0280605 P1 Sep. 28, 2017

(51) Int. Cl.
*A01H 5/02* (2018.01)

(52) U.S. Cl.
USPC ..... Plt./310

(58) Field of Classification Search
USPC ..... Plt./310
See application file for complete search history.

(56) References Cited

PUBLICATIONS

UPOV hit on *Dietes* plant named 'DI2', AU PBR 2015048, applied Mar. 24, 2015.*

* cited by examiner

*Primary Examiner* — Anne Marie Grunberg
(74) *Attorney, Agent, or Firm* — Samuel R. McCoy, Jr.

(57) ABSTRACT

'DI2' is a distinctive cultivar of *Dietes bicolor* plant which is characterized by the combination of fine-textured foliage and low seed production. The new variety propagates successfully by division and tissue culture and has shown to be uniform and stable in the resulting generations from asexual propagation.

1 Drawing Sheet

Latin name of the genus and species: The Latin name of the genus and species of the novel variety disclosed herein is *Dietes bicolor.*

Variety denomination: The inventive variety of *Dietes bicolor* disclosed herein has been given the variety denomination 'DI2'.

BACKGROUND OF THE INVENTION

Parentage: 'DI2' is a seedling selection of unknown origin which resulted from an open-pollination and seedling selection process carried out by the inventor at a commercial breeding facility in Clarendon, NSW, Australia. In 2010, a number of unnamed *Dietes bicolor* seedlings, developed by the same inventor, were grown in close proximity to one another in order to encourage open cross pollination. In 2011, approximately 100 seeds were collected from these plants. The resulting seedlings were grown to maturity for further observation and, after the first flowering, a small number of plants were observed to produce fewer seeds by comparison with the original unnamed seedlings. One progeny in particular was observed to exhibit narrow foliage, in combination with reduced seed head production and very few seeds. This new and distinctive cultivar was given the name 'DI2'.

Asexual Reproduction: 'DI2' was first asexually propagated in early 2011 by rhizome division in Clarendon, NSW, Australia and has since been asexually reproduced by meristematic tissue culture propagation. The distinctive characteristics of the inventive 'DI2' variety have proven to be stable through five generations and clones so produced maintain the distinguishing characteristics of the original plant.

SUMMARY OF THE INVENTION

The following traits have been repeatedly observed and represent the characteristics of the new cultivar. These characteristics, in combination, distinguish 'DI2' as a distinct cultivar of *Dietes bicolor.*

1. 'DI2' exhibits low seed production; and
2. 'DI2' exhibits fine-textured foliage.

BRIEF DESCRIPTION OF THE FIGURES

The figure illustrates, as true as is reasonably possible to obtain in color photographs of this type, an exemplary 'DI2' specimen on the left, with an exemplary specimen of the species, *Dietes bicolor*, on the right. These 12 month old plants were grown outdoors in 6 inch nursery containers at a commercial plant breeding facility in Clarendon, NSW, Australia. Inset in the bottom left-hand corner of the figure is an exemplary flower of 'DI2'.

BOTANICAL DESCRIPTION OF THE PLANT

The following is a detailed botanical description of a new and distinct variety of a *Dietes bicolor* ornamental plant known as 'DI2'. Plant observations were made on plants grown in Clarendon, NSW, Australia. Unless indicated otherwise, the descriptions disclosed herein are based upon observations made in March 2016 of 24 month old 'DI2' plants. These plants were grown outdoors, in full sun, in 12 inch nursery pots filled with soilless potting media, maintained with granular slow release fertilizer and regularly watered with overhead irrigation. No pest and disease measures were taken.

Those skilled in the art will appreciate that certain characteristics will vary with older or, conversely, younger plants. 'DI2' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, Fourth Edition. Note that generic color descriptions such as 'green' do not exist in the R.H.S. charts and the corresponding R.H.S. colors are quoted.

A botanical description of 'DI2' and comparisons with the seed parent and several similar varieties of common knowledge are provided below.

General plant description:

*Plant habit.*—Grass-like herbaceous perennial with erect to semi-erect foliage; rhizomatous plant forming a dense tussock.

*Height.*—80 cm.

*Width.*—80 cm.

*Hardiness.*—USDA Zone 8 to 11.

*Propagation.*—Propagation is accomplished by dividing the rhizomatous crown of the plant and also by way of meristematic tissue culture propagation.

*Crop time.*—Time to develop a rooted cutting is approximately 8 weeks, from division. An average crop time is approximately 8 to 10 months to produce a mature and marketable one gallon nursery container, beginning with a rooted cutting.

*Environmental tolerances.*—Tolerates Mediterranean to subtropical climates; full sun to partial shade; poor to fertile soils; drought tolerant once established.

*Pest and disease susceptibility or resistance.*—No known pest or disease problems.

Roots: Rhizomes with fine, fibrous roots.

Stems:

*Branching habit.*—Acaulescent, rhizomatous plant with shoots emerging upright at close to 90 degrees from the soil surface.

*Shoots.*—Quantity — Approximately ten. Strength — Very Strong. Dimensions, 5 days after emerging — 30 to 45 mm tall and 17 mm in diameter. Cross-section — Round to slightly flattened. Apex — Acute. Color — A combination of yellow-green, RHS 147B, and orange-white 159D. Texture and pubescence — Smooth and glabrous.

Foliage:

*Type.*—Evergreen.

*Shape.*—Ensiform.

*Division.*—Simple.

*Arrangement.*—Equitant.

*Attachment.*—Sheathed.

*Apex.*—Subulate.

*Base.*—Sheathed attachment to the culm.

*Margins.*—Entire.

*Mature leaf dimensions.*—10.5 mm wide and 800 mm long, on average. The leaf thickness is 1.3 mm, on average.

*Juvenile foliage color, adaxial & abaxial surfaces.*—Green, RHS 138C.

*Mature foliage color, adaxial & abaxial surfaces.*—Green, RHS 137B.

*Venation.*—Parallel.

*Vein color, adaxial surfaces.*—Green, RHS 137C.

*Vein color, abaxial surfaces.*—Yellow-green, RHS 144B.

*Texture, adaxial surface.*—Smooth and glabrous.

*Texture, abaxial surface.*—Smooth and densely pubescent.

Inflorescence:

*Type.*—Cymose branched inflorescence.

*Natural flowering season.*—Heaviest blooming is observed in summer, with sporadic blooms in spring and fall.

*Overall dimensions.*—Up to 800 mm long and 200 mm wide.

*Quantity.*—Inflorescences may potentially arise from every shoot.

*Peduncle.*—Dimensions — Up to 200 to 300 mm long and 4 mm in diameter. Attitude — Erect to approximately 30 degrees from erect. Strength — Very strong. Texture — Smooth. Color — Green, RHS 138A.

Bud:

*Dimensions.*—Approximately 35 mm long and 6 mm wide.

*Bud shape.*—Narrow, ovoid.

*Bud color.*—A combination of yellow-green, RHS 147A, and yellow, RHS 7D.

*Rate of bud opening.*—Slow.

*Bract.*—Buds are enclosed in a single lanceolate bract; color is green, RHS 138A; texture is smooth; glabrous.

Flower:

*Quantity.*—Approximately 6 to 8 flowers per inflorescence.

*Shape.*—Shallow cup.

*Persistence.*—Non-persistent.

*Lastingness.*—One to two days.

*Aspect.*—Upward and outward.

*Fragrance.*—Non-fragrant.

*Pedicels.*—Dimensions — 20 to 40 mm long and 4 mm in diameter. Attitude — Erect to semi-erect. Strength — Very strong. Texture — Smooth. Color — Green, RHS 138A.

*Perianth.*—General description — Perianth is comprised of six tepals; 3 inner tepals and 3 larger outer tepals. Dimensions — Approximately 65 mm in diameter and 35 mm deep, from the base of the receptacle. Tepals — Quantity — Three inner tepals and three larger outer tepals. Inner tepals — Dimensions — 28 mm long and 13 mm wide. Shape — Elliptical. Apex — Obtuse. Base — Truncate. Tepal reflex — Slightly incurved to slightly reflexed. Margin — Entire; occasionally emarginate. Not undulated. Texture and pubescence — Smooth and glabrous. Color when fully opened, upper surface — Yellow, RHS 7D. Color when fully opened, lower surface — Yellow, RHS 7D. Outer tepals — Dimensions — 30 mm long and 23 mm wide. Shape — Trilobate; lobes are broadly ovate. Apex — Obtuse to emarginate. Base — Truncate. Tepal reflex — Slightly incurved to slightly reflexed. Margin — Entire; slightly undulated. Texture and pubescence — Smooth and glabrous. Color when fully opened, upper surface — Yellow, RHS 7D, with nectar guides consisting of an irregular semi-circular blotch of approximately 6 mm long and 4.5 mm wide near the base of each tepal, colored brown RHS 200B and bordered with greyed-orange, RHS 173B, and also several rows of fine dots positioned between the proximal end of the tepal and the irregular blotches. Dots are approximately 0.25 mm in diameter and colored greyed-orange 173B. Color when fully opened, lower surface — Yellow, RHS 7D, with nectar guides consisting of an irregular semi-circular blotch of approximately 6 mm long and 4.5 mm wide near the base of each tepal, colored brown RHS 200B and bordered with greyed-orange, RHS 173B, and also several rows of fine dots positioned between the proximal end of the tepal and the irregular blotches. Dots are approximately 0.25 mm in diameter and colored greyed-orange 173B.

Reproduction organs:

*Stamens.*—Quantity — Three. Filament — Approximately 6 to 7 mm long and 0.25 in diameter; color is yellow, RHS 7D. Anther — Two-lobed; oblong to linear; basifixed; approximately 4.5 mm long and 1 mm in diameter; color is yellow, RHS 7D. Pollen — Scarce; color is closest to yellow, RHS 7D.

*Pistil.*—Petaloid pistil; style is comprised of 3 petal-like branches of approximately 16 mm long and 8 wide, with bifurcate to emarginate apices; margins are entire; color is yellow, RHS 7D. Stigma is undetected. Ovary is inferior; shape is narrow linear; 15 mm long and 3 mm in diameter.

Seed:

*Quantity.*—Very few seeds produced.

*Shape.*—Irregular; ovoid.

*Dimensions.*—Approximately 3 mm by 3 mm.

*Color.*—Pale yellow to cream, closest to yellow-white RHS 158B.

*Texture.*—Smooth.

COMPARISONS WITH THE PARENT PLANTS

The actual antecedents are unknown, so a parental comparison is not possible.

COMPARISONS WITH THE MOST SIMILAR VARIETY OF COMMON KNOWLEDGE

Plants of the new cultivar 'DI2' may be distinguished from the commercial variety, *Dietes bicolor* 'Nola Alba' (U.S. Pat. No. 21,460), by the following combination of characteristics:

1. 'DI2' exhibits narrow foliage, whereas 'Nola Alba' exhibits wide foliage.
2. 'DI2' exhibits yellow flowers, whereas 'Nola Alba' exhibits white flowers.

That which is claimed is:

1. A new and distinct variety of *Dietes bicolor* plant named 'DI2', substantially as described and illustrated herein.

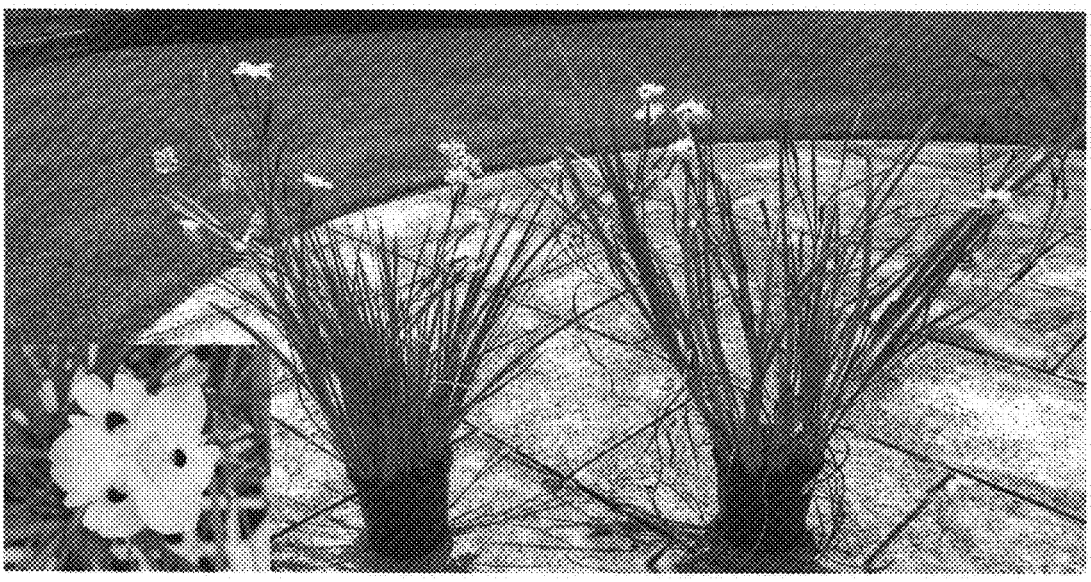

* * * * *